United States Patent [19]

Minami et al.

[11] Patent Number: 4,650,798

[45] Date of Patent: Mar. 17, 1987

[54] ANTIARRHYTHMIC 2,2-DIALKYL-1-(AMINOALKYL)-SPIRO[CHROMAN-4,4'-IMIDAZOLIDINE]-2',5'-DIONES

[75] Inventors: Norio Minami, Sakuramura; Masayuki Mathukura, Yatabemachi; Koichiro Ueda, Hasuda; Satoru Tanaka, Abiko; Toshiji Igarashi, Toyosato, all of Japan

[73] Assignee: Eisai Co., Ltd., Tokyo, Japan

[21] Appl. No.: 695,152

[22] Filed: Jan. 25, 1985

[30] Foreign Application Priority Data

Jan. 30, 1984 [JP] Japan .................................. 59-13442

[51] Int. Cl.[4] ................. A61K 31/415; A61K 31/535; C07D 405/14; C07D 413/14

[52] U.S. Cl. ..................... 514/227; 514/240; 514/253; 514/256; 514/278; 514/365; 514/372; 514/374; 514/378; 514/389; 544/70; 544/230; 546/15; 548/147; 548/214; 548/216; 548/240; 548/309

[58] Field of Search ............... 548/309, 147, 214, 216, 548/240; 544/139, 370, 70, 230; 546/196, 15; 514/227, 253, 320, 389, 240, 256, 278, 365, 372, 374, 378

[56] References Cited

FOREIGN PATENT DOCUMENTS 2455046 11/1980 France ................................ 548/309

Primary Examiner—Henry R. Jiles
Assistant Examiner—Kurt G. Briscoe
Attorney, Agent, or Firm—Flynn, Thiel, Boutell & Tanis

[57] ABSTRACT

1-Substituted-spiro[chroman-4,4'-imidazolidine]-2',5'-dione compounds are useful for treating arrhythmia.

11 Claims, No Drawings

ANTIARRHYTHMIC 2,2-DIALKYL-1-(AMINOALKYL)-SPIRO[CHROMAN-4,4'-IMIDAZOLIDINE]-2',5'-DIONES

The present invention relates to hydantoin derivatives having excellent medicinal effects. More particularly, the invention relates to hydantoin derivatives having the following general formula and pharmaceutically acceptable acid addition salts thereof:

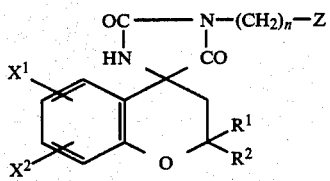

wherein $X^1$ and $X^2$ can be the same or different and each represents a hydrogen atom, a halogen atom, a lower alkyl group, a lower alkoxy group, trifluoromethyl, trifluoroethoxy or a nitro group, or $X^1$ and $X^2$ together form an alkylenedioxy group (—O—R—O—) connected to adjacent carbon atoms in the ring; $R^1$ and $R^2$ can be the same or different and each represents a hydrogen atom or a lower alkyl group, or $R^1$ and $R^2$ together with the carbon atom to which they are bonded form a $C_5$ or $C_6$ cycloalkyl group; Z represents (a) a group of the formula:

in which $R^3$ and $R^4$ can be the same or different and each represents a hydrogen atom, a lower alkyl group, a hydroxyalkyl group or a substituted or unsubstituted aralkyl group, or $R^3$ and $R^4$ together with the nitrogen atom to which they are bonded, form a $C_5$ or $C_6$ saturated heterocyclic group, which heterocyclic ring can further contain an oxygen atom or a nitrogen atom and may have a substituent such as a C1–C6 lower alkyl and an aryl on the nitrogen atom, (b) a group of the formula:

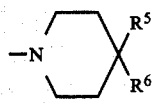

in which $R^5$ and $R^6$ can be the same or different and each represents a hydrogen atom, a phenyl group or a group of the formula: —$OR^7$ ($R^7$ being a hydrogen atom, an acyl group, a lower alkyl group or a substituted or unsubstituted aralkyl group) or $R^5$ and $R^6$ together with the carbon atom to which they are bonded form a 4-membered or 5-membered cyclic group containing two oxygen atoms, or $R^5$ and $R^6$ together form a group of the formula: =O, or (c) a group of the formula:

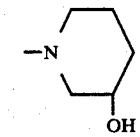

and n represents an integer of 2 to 7; processes for the production thereof; and antiarrhythmic agents containing them as an active ingredient.

Definitions of terms used herein will now be described.

The term "lower" refers to a group having 1 to 6 carbon atoms unless otherwise stated.

The term "lower alkyl group" in the definition of $X^1$, $X^2$, $R^1$, $R^2$, $R^3$, $R^4$ and $R^7$ includes straight-chain and branched alkyl groups, such as methyl, ethyl, propyl, isopropyl, butyl, isobutyl, pentyl, isopentyl and hexyl groups. Among them, alkyl groups having 1 to 6 carbon atoms are preferred and those having 1 to 3 carbon atoms are particularly preferred.

The term "halogen atom" in the definition of $X^1$ and $X^2$ includes, for example, fluorine, chlorine and bromine atoms.

The term "lower alkoxy group" in the definition of $X^1$ and $X^2$ includes straight-chain and branched lower alkoxy groups such as methoxy, ethoxy, propoxy, isopropoxy, butoxy, isobutoxy, pentyloxy, isopentyloxy and hexyloxy groups. The alkylenedioxy groups formed by $X^1$ and $X^2$ together with adjacent carbon atom(s) on the benzene ring include, for example, methylenedioxy and ethylenedioxy groups.

The term "aralkyl groups" in the definition of $R^3$ and $R^4$ includes, for example, benzyl, phenethyl and 3,4-dimethoxyphenethyl groups.

The term "C5 or C6 saturated heterocyclic group" includes for example morpholino and piperazyl. Piperazyl group may have a substituent on the aryl portion, such as an aryl group and C1 to C6 lower alky group.

The pharmaceutically acceptable acid addition salts of the hydantoin derivatives of the present invention include salts thereof with inorganic acids such as phosphoric acid, hydrochloric acid, sulfuric acid, hydrogen bromide and hydrogen iodide, and organic acids such as fumaric acid, oxalic acid, acetic acid, methanesulfonic acid, lactic acid, citric acid, tartaric acid and succinic acid.

Typical examples of processes for producing the intended compounds (I) of the present invention will now be given. These processes are shown by the following flow sheet:

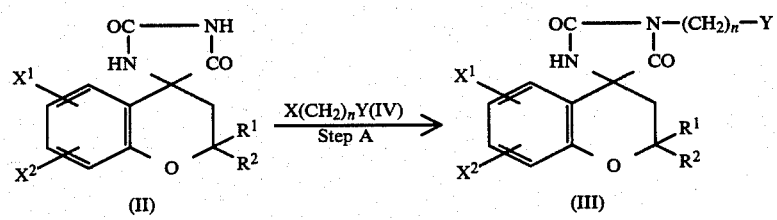

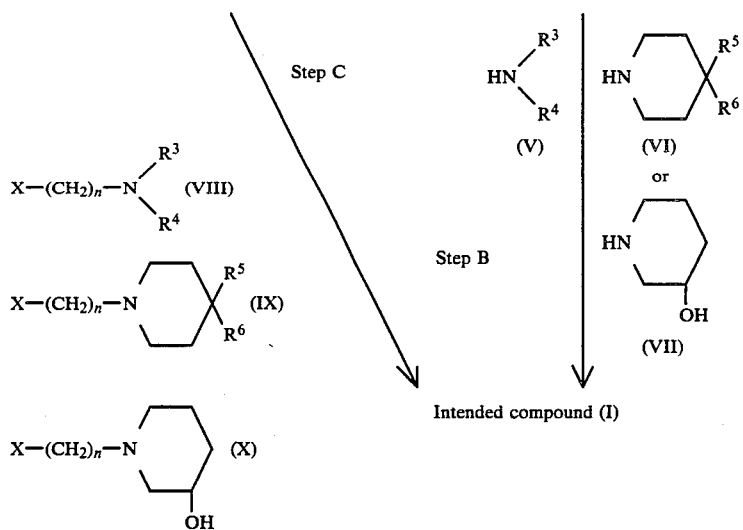

-continued

Intended compound (I)

wherein X and Y each represents a halogen atom, such as chlorine or bromine, and $X^1$, $X^2$, $R^1$, $R^2$, $R^5$, $R^6$ and n have the same meanings as set forth above.

Namely, a compound of general formula (II) is reacted with a compound of general formula (IV) to obtain a compound of general formula (III) (step A) and then the compound of formula (III) is reacted with a compound of general formula (V), (VI) or (VII) to obtain an intended compound of formula (I) (step B).

In another process, a compound of general formula (II) is reacted with a compound of general formula (VIII), (IX) or (X) to form an intended compound of formula (I) (step C).

Now, the description will be made on the respective reaction steps.

REACTION STEP A

Process 1

A compound of general formula (II) is reacted with sodium hydride, potassium hydride, calcium hydride or sodium amide in a solvent such as dimethylformamide, dimethylacetamide, dimethyl sulfoxide, dioxane, diethyl ether, tetrahydrofuran or acetonitrile under cooling with ice or at room temperature and the reaction product is reacted with a compound of general formula (IV) to obtain a compound of general formula (III).

Process 2

A compound of general formula (II) is reacted with a sodium or potassium alcoholate such as sodium methylate, sodium ethylate, potassium methylate or potassium ethylate in a solvent such as methanol, ethanol, isopropanol, butanol, dimethylformamide, dimethylacetamide, diethyl ether, dioxane, tetrahydrofuran or acetonitrile under cooling with ice or at room temperature and the reaction product is reacted with a compound (IV) to obtain a compound of general formula (III).

Process 3

A compound such as potassium carbonate, sodium carbonate, potassium hydroxide, sodium hydroxide, triethylamine, diisopropylethylamine, dimethylaminopyridine or pyridine is added to a compound of general formula (II) in a solvent such as dimethylformamide, dimethylacetamide, dimethyl sulfoxide, diethyl ether, dioxane, tetrahydrofuran, acetonitrile, acetone, methyl ethyl ketone, methanol, ethanol, isopropanol or butanol. The resulting compound is reacted with a compound of general formula (IV) at room temperature or under reflux to obtain a compound of general formula (III).

REACTION STEP B

Process 1

A compound of general formula (V), (VI) or (VII) is added to a compound of general formula (III) in a solvent such as dimethylformamide, dimethylacetamide, dimethyl sulfoxide, diethyl ether, dioxane, tetrahydrofuran or acetonitrile. Then, a compound such as sodium hydride, potassium hydride, calcium hydride or sodium amide is added thereto and the reaction is carried out under cooling with ice or under reflux to obtain an intended compound of formula (I).

Process 2

A compound of general formula (V), (VI) or (VII) is added to a compound of general formula (III) in a solvent such as methanol, ethanol, isopropanol, butanol, dimethylformamide, dimethylacetamide, diethyl ether, dioxane, dimethyl sulfoxide, tetrahydrofuran or acetonitrile. Then, a sodium or potassium alcoholate such as sodium methylate, sodium ethylate, potassium methylate or potassium ethylate is added thereto and the reaction is carried out under cooling with ice or under reflux to obtain an intended compound of formula (I).

Process 3

A compound of general formula (V), (VI) or (VII) is added to a compound of general formula (III) in a solvent such as chloroform, dichloromethane, dichloroethane, acetone, methyl ethyl ketone, methanol, ethanol, isopropanol, butanol, dimethylformamide, dimethylacetamide, diethyl ether, dioxane, tetrahydrofuran or dimethyl sulfoxide. Then, a compound such as potassium carbonate, sodium carbonate, potassium hydroxide, sodium hydroxide, triethylamine, diisopropylethylamine, dimethylaminopyridine or pyridine is added thereto and the reaction is carried out at room temperature or under reflux to obtain an intended compound of formula (I).

REACTION STEP C

Process 1

A compound of general formula (II) is reacted with sodium hydride, potassium hydride, calcium hydride or sodium amide in a solvent such as dimethylformamide, dimethylacetamide, dimethyl sulfoxide, dioxane, diethyl ether, tetrahydrofuran or acetonitrile under cooling with ice or at room temperature. A compound of general formula (VIII), (IX) or (X) is added thereto and the reaction is carried out at room temperature or under reflux to obtain an intended compound of formula (I).

Process 2

A compound of the general formula (II) is reacted with a sodium or potassium alcoholate such as sodium methylate, sodium ethylate, potassium methylate or potassium ethylate in a solvent such as methanol, ethanol, isopropanol, butanol, dimethylformamide, dimethylacetamide, diethyl ether, dioxane, tetrahydrofuran or acetonitrile under cooling with ice or at room temperature. A compound of general formula (VIII), (IX) or (X) is added to the reaction product and the reaction is carried out at room temperature or under reflux to obtain an intended compound of formula (I).

Process 3

A base such as potassium carbonate, sodium carbonate, potassium hydroxide, sodium hydroxide, triethylamine, diisopropylethylamine, pyridine or dimethylaminopyridine and a compound of general formula (VIII), (IX) or (X) are added to a compound of general formula (II) in a solvent such as dimethylformamide, dimethylacetamide, dimethyl sulfoxide, diethyl ether, dioxane, tetrahydrofuran, acetonitrile, acetone, methyl ethyl ketone, methanol, ethanol, isopropanol or butanol and the reaction is carried out at room temperature or under reflux to obtain an intended compound of formula (I).

Examples of the compounds provided by the present invention will be given below. These examples do not limit the scope of the present invention, but rather, are intended to facilitate an understanding of the invention. The compounds listed below are in their free forms. The compounds of formula (I) of the present invention include all of their stereoisomers and optical isomers which might be formed when they have asymmetric carbon atom(s) the number of which varies depending on the substituents.

2,2-dimethyl-6-fluoro-1'-[3-(4-hydroxypiperidino)propyl]spiro[chroman-4,4'-imidazolidine]-2',5'-dione,
6-chloro-2-methyl-1'-[3-(4-phenylpiperidino)propyl]spiro[chroman-4,4'-imidazolidine]-2',5'-dione,
6-chloro-2-methyl-1'-[3-(4-hydroxy-4-phenylpiperidino)propyl]spiro[chroman-4,4'-imidazolidine]-2',5'-dione,
6-fluoro-2-methyl-1'-[3-(4-phenylpiperidino)propyl]spiro[chroman-4,4'-imidazolidine]-2',5'-dione,
6-fluoro-1'-[3-(4-phenylpiperidino)propyl]spiro[chroman-4,4'-imidazolidine]-2',5'-dione,
6-chloro-2,2-dimethyl-1'-[4-(4-phenylpiperidino)butyl]spiro[chroman-4,4'-imidazolidine]-2',5'-dione,
2,2-dipropyl-6-fluoro-1-[3-(4-hydroxypiperidino)propyl]spiro[chroman-4,4'-imidazolidine]-2',5'-dione,
6-chloro-2,2-dimethyl-1'-[3-(4-phenylpiperidino)propyl]spiro[chroman-4,4'-imidazolidine]-2',5'-dione,
6-chloro-2,2-dimethyl-1'-[3-(4-hydroxy-4-phenylpiperidino)propyl]spiro[chroman-4,4'-imidazolidine]-2',5'-dione,
2,6-dimethyl-1'-[3-(4-phenylpiperidino)propyl]spiro[chroman-4,4'-imidazolidine]-2',5'-dione,
6-methoxy-2-methyl-1'-[3-(4-phenylpiperidino)propyl]spiro[chroman-4,4-imidazolidine]-2',5'-dione,
2,2-dimethyl-6-methoxy-1'-[3-(4-phenylpiperidino)propyl]spiro[chroman-4,4'-imidazolidine]-2',5'-dione,
2,2-dibutyl-1'-[3-(4-phenylpiperidino)propyl]spiro[chroman-4,4'-imidazolidine]-2',5'-dione,
2,2-dibutyl-1'-[3-(4-hydroxy-4-phenylpiperidino)propyl]spiro[chroman-4,4'-imidazolidine]-2',5'-dione,
6,8-dichloro-2,2-dimethyl-1'-[3-(4-hydroxypiperidino)propyl]spiro[chroman-4,4'-imidazolidine]-2',5'-dione,
6,8-dichloro-1'-[3-(4-hydroxypiperidino)propyl]spiro[chroman-4,4'-imidazolidine]-2',5'-dione,
6,8-dichloro-1'-[4-(4-hydroxypiperidino)butyl]spiro[chroman-4,4'-imidazolidine]-2',5'-dione,
6,8-dichloro-1'-[3-(4-phenylpiperidino)propyl]spiro[chroman-4,4'-imidazolidine]-2',5'-dione,
8-chloro-2,2-dimethyl-1'-[3-(4-phenylpiperidino)propyl]spiro[chroman-4,4'-imidazolidine]-2',5'-dione,
2,2-diethyl-6-fluoro-1'-[3-(4-hydroxypiperidino)propyl]spiro[chroman-4,4'-imidazolidine]-2',5'-dione,
2,2-diethyl-6-fluoro-1'-[4-(4-hydroxypiperidino)butyl]spiro[chroman-4,4'-imidazolidine]-2',5'-dione,
6-fluoro-1'-[3-(4-hydroxypiperidino)propyl]spiro[chroman-4,4'-imidazolidine]-2',5'-dione,
6-fluoro-1'-[4-(4-hydroxypiperidino)butyl]spiro[chroman-4,4'-imidazolidine]-2',5'-dione,
6-fluoro-1'-[5-(4-hydroxypiperidino)pentyl]spiro[chroman-4,4'-imidazolidine]-2',5'-dione,
6-chloro-1'-[3-(4-phenylpiperidino)propyl]spiro[chroman-4,4'-imidazolidine]-2',5'-dione,
6-methoxy-1'-[3-(4-hydroxypiperidino)propyl]spiro[chroman-4,4'-imidazolidine]-2',5'-dione,
2,2-dimethyl-6-methoxy-1'-[3-(4-hydroxypiperidino)propyl]spiro[chroman-4,4'-imidazolidine]-2',5'-dione,
2,2-dimethyl-6-methyl-1'-[3-(4-hydroxypiperidino)propyl]spiro[chroman-4,4'-imidazolidine]-2',5'-dione,
2,2-dimethyl-6-methyl-1'-[3-(4-phenylpiperidino)propyl]spiro[chroman-4,4'-imidazolidine]-2',5'-dione,
2,2-dimethyl-6-methyl-1'-[3-(4-methoxypiperidino)propyl]spiro[chroman-4,4'-imidazolidine]-2',5'-dione,
2,2-dimethyl-6-methoxy-1'-[3-(4-acetoxypiperidino)propyl]spiro[chroman-4,4'-imidazolidine]-2',5'-dione,
2,2-dimethyl-6-fluoro-1'-[3-(4-propoxypiperidino)propyl]spiro[chroman-4,4'-imidazolidine]-2',5'-dione,
2,2-dipropyl-6-fluoro-1'-[3-(4-hydroxypiperidino)propyl]spiro[chroman-4,4'-imidazolidine]-2',5'-dione,
2,2-dipentyl-6-fluoro-1'-[4-(4-hydroxypiperidino)butyl]spiro[chroman-4,4'-imidazolidine]-2',5'-dione,
2,2-dimethyl-6-fluoro-1'-[3-(4-methoxypiperidino)propyl]spiro[chroman-4,4'-imidazolidine]-2',5'-dione,
6-fluoro-1'-[3-(4-methoxypiperidino)propyl]spiro[chroman-4,4'-imidazolidine]-2',5'-dione,
6-chloro-2,2-dimethyl-1'-[3-(4-hydroxypiperidino)propyl]spiro[chroman-4,4'-imidazolidine]-2',5'-dione,
6-chloro-2,2-dimethyl-1'-[3-(4-ethoxypiperidino)propyl]spiro[chroman-4,4'-imidazolidine]-2',5'-dione,
6-chloro-2,2-dimethyl-1'-[4-(4-hydroxypiperidino)butyl]spiro[chroman-4,4'-imidazolidine]-2',5'-dione,
6-bromo-2,2-dimethyl-1'-[3-(4-hydroxypiperidino)propyl]spiro[chroman-4,4'-imidazolidine]-2',5'-dione, 6-bromo-1'-[3-(4-hydroxypiperidino)propyl]spiro[chroman-4,4'-imidazolidine]-2',5'-dione,
6-bromo-2,2-dimethyl-1'-[2-(4-hydroxypiperidino)ethyl]spiro[chroman-4,4'-imidazolidine]-2',5'-dione,
6-bromo-2,2-diethyl-1'-[4-(4-hydroxypiperidino)butyl]spiro[chroman-4,4'-imidazolidine]-2',5'-dione,
2,2-dimethyl-7-methoxy-8-methyl-1'-[3-(4-hydroxypiperidino)propyl]spiro[chroman-4,4'-imidazolidine]-2',5'-dione,
7-methoxy-8-methyl-1'-[3-(4-hydroxy-4-phenylpiperidino)propyl]spiro[chroman-4,4'-imidazolidine]-2',5'-dione,
6-chloro-1'-[3-(4-hydroxypiperidino)propyl]spiro[chroman-4,4'-imidazolidine]-2',5'-dione,
2,2-dihexyl-6-fluoro-1'-[3-(4-acetoxypiperidino)propyl]spiro[chroman-4,4'-imidazolidine]-2',5'-dione,
2,2-dimethyl-6-fluoro-1'-[3-(4-hydroxy-4-phenylpiperidino)propyl]spiro[chroman-4,4'-imidazolidine]-2',5'-dione,
2,2-dimethyl-6-fluoro-1'-[3-(4-acetoxy-4-phenylpiperidino)propyl]spiro[chroman-4,4'-imidazolidine]-2',5'-dione,
8-chloro-1'-[3-(4-hydroxypiperidino)propyl]spiro[chroman-4,4'-imidazolidine]-2',5'-dione,
8-chloro-1'-[3-(4-acetoxypiperidino)propyl]spiro[chroman-4,4'-imidazolidine]-2',5'-dione,
2,2-dimethyl-6-fluoro-1'-{3-[4-(2-chlorobenzyloxy)piperidinol]propyl}spiro[chroman-4,4'-imidazolidine]-2',5'-dione,
2,2-dimethyl-6-fluoro-1'-{3-[4-(4-chlorobenzyloxy)piperidino]propyl}spiro[chroman-4,4'-imidazolidine]-2',5'-dione,
2,2-dimethyl-6-fluoro-1'-[2-(4-hydroxypiperidino)ethyl]spiro[chroman-4,4'-imidazolidine]-2',5'-dione,
2,2-dimethyl-6-fluoro-1'-[2-(4-acetoxypiperidino)ethyl]spiro[chroman-4,4'-imidazolidine]-2',5'-dione,
6-chloro-1'-[4-(4-acetoxypiperidino)butyl]spiro[chroman-4,4'-imidazolidine]-2',5'-dione,
6-dichloro-2,2-diethyl-1'-[3-(4-hydroxypiperidino)propyl]spiro[chroman-4,4'-imidazolidine]-2',5'-dione,
6-chloro-2,2-diethyl-1'-[3-(4-phenylpiperidino)propyl]spiro[chroman-4,4'-imidazolidine]-2',5'-dione,
6-chloro-2,2-diethyl-1'-[2-(4-hydroxypiperidino)ethyl]spiro[chroman-4,4'-imidazolidine]-2',5'-dione,
2,2-dimethyl-6-fluoro-1'-[4-(4-hydroxypiperidino)butyl]spiro[chroman-4,4'-imidazolidine]-2',5'-dione,
2,2-dimethyl-6-fluoro-1'-[4-(4-acetoxypiperidino)butyl]spiro[chroman-4,4'-imidazolidine]-2',5'-dione,
2,2-dimethyl-6-fluoro-1'-[4-(4-phenylpiperidino)butyl]spiro[chroman-4,4'-imidazolidine]-2',5'-dione,
2,2-dimethyl-6-fluoro-1'-[3-(4-oxopiperidino)propyl]spiro[chroman-4,4'-imidazolidine]-2',5'-dione,
2,2-dibutyl-6-fluoro-1'-[3-(4-oxopiperidino)propyl]spiro[chroman-4,4'-imidazolidine]-2',5'-dione,
2,2-dimethyl-6-fluoro-1'-[3-(4-acetoxypiperidino)propyl]spiro[chroman-4,4'-imidazolidine]-2',5'-dione,
1'-[3-(4-hydroxypiperidino)propyl]spiro[chroman-4,4'-imidazolidine]-2',5'-dione,
1'-[3-(4-hydroxy-4-phenylpiperidino)propyl]spiro[chroman-4,4'-imidazolidine]-2',5'-dione,
2,2-dimethyl-6-fluoro-1'-(3-piperidinopropyl)spiro[chroman-4,4'-imidazolidine]-2',5'-dione,
cyclohexane<spiro-2>-6-chloro-1'[3-(4-hydroxypiperidino)propyl]spiro[chroman-4,4'-imidazolidine]-2',5'-dione,
cyclopentane<spiro-2>-6-fluoro-1'-[3-(4-hydroxypiperidino)propyl]spiro[chroman-4,4'-imidazolidine]2',5'-dione,
2,2-dimethyl-6-fluoro-1'-[3-(4-phenylpiperidino)propyl]spiro[chroman-4,4'-imidazolidine]-2',5'-dione,
2,2-dimethyl-6-fluoro-1'-[3-(4-ethylenedioxypiperidino)propyl]spiro[chroman-4,4'-imidazolidine]-2',5'-dione,
2,2-dimethyl-6-fluoro-1'-[3-(3-hydroxypiperidino)propyl]spiro[chroman-4,4'-imidazolidine]-2',5'-dione,
2,2-dimethyl-6-fluoro-1'-[6-(4-hydroxypiperidino)hexyl]spiro[chroman-4,4'-imidazolidine]-2',5'-dione,
6-chloro-2,2-dimethyl-1'-[4-(4-acetoxypiperidino)butyl]spiro[chroman-4,4'-imidazolidine]-2',5'-dione,
6-chloro-2,2-dimethyl-1'-[5-(4-hydroxypiperidino)pentyl]spiro[chroman-4,4'-imidazolidine]-2',5'-dione,
6-chloro-2,2-dimethyl-1'-[6-(4-hydroxypiperidino)hexyl]spiro[chroman-4,4'-imidazolidine]-2',5'-dione,
6-chloro-2,2-dimethyl-1'-[7-(4-hydroxypiperidino)heptyl]spiro[chroman-4,4'-imidazolidine]-2',5'-dione,
6-chloro-2,2-dibutyl-1'-[3-(4-hydroxypiperidino)propyl]spiro[chroman-4,4'-imidazolidine]-2',5'-dione,
cyclohexane<spiro-2>-6-methoxy-1'-[3-(4-hydroxypiperidinol)propyl]spiro[chroman-4,4'-imidazolidine]-2',5'-dione,
6-chloro-2-methyl-1'-(2-dimethylaminoethyl)spiro[chroman-4,4'-imidazolidine]-2',5'-dione,
6-chloro-2-methyl-1'-(3-dimethylaminopropyl)spiro[chroman-4,4'-imidazolidine]-2',5'-dione,
6-fluoro-2-methyl-1'-(2-methylaminoethyl)spiro[chroman-4,4'-imidazolidine]-2',5'-dione,
6-chloro-2-methyl-1'-(2-diethylaminoethyl)spiro[chroman-4,4'-imidazolidine]-2',5'-dione,
2,2-dimethyl-6-chloro-(3-dimethylaminopropyl)spiro[chroman-4,4'-imidazolidine]-2',5'-dione,
2-ethyl-6-chloro-(3-dimethylaminopropyl)spiro[chroman-4,4'-imidazolidine]-2',5'-dione,
cyclohexane<spiro-2>-6-chloro-1'-(3-dimethylaminopropyl)spiro[chroman-4,4'-imidazolidine]-2',5'-dione,
2,2-dimethyl-6-bromo-1'-(3-dimethylaminopropyl)spiro[chroman-4,4'-imidazolidine]-2',5'-dione,
cyclopentane<spiro-2>-6-chloro-1'-(3-dimethylaminopropyl)spiro[chroman-4,4'-imidazolidine]-2',5'-dione,
2,2-dimethyl-6-fluoro-8-nitro-1'-(3-dimethylaminopropyl)spiro[chroman-4,4'-imidazolidine]-2',5'-dione,
2,2-dimethyl-6-fluoro-1'-(3-dimethylaminopropyl)spiro[chroman-4,4'-imidazolidine]-2',5'-dione,
6-fluoro-2-methyl-1'-(3-dimethylaminopropyl)spiro[chroman-4,4'-imidazolidine]-2',5'-dione,
2,2-dimethyl-6-fluoro-1'-(2-diethylaminoethyl)spiro[chroman-4,4'-imidazolidine]-2',5'-dione,
2,2-dimethyl-6-fluoro-1'-(2-diisopropylaminoethyl)spiro[chroman-4,4'-imidazolidine]-2',5'-dione,
2,2-dimethyl-6-fluoro-1'-(3-diethylaminopropyl)spiro[chroman-4,4'-imidazolidine]-2',5'-dione,
2,2'-dimethyl-6-fluoro-1'-(3-n-propylaminopropyl)spiro[chroman-4,4'-imidazolidine]-2',5'-dione,
2,2-dimethyl-1'-(3-dimethylaminopropyl)spiro[chroman-4,4'-imidazolidine]-2',5'-dione,
6-chloro-2,2-di-n-propyl-1'-(3-dimethylaminopropyl)spiro[chroman-4,4'-imidazolidine]-2',5'-dione,
2,2-dimethyl-6-chloro-1'-(4-dimethylaminobutyl)spiro[chroman-4,4'-imidazolidine]-2',5'-dione,
2,2-dimethyl-6-chloro-1'-(5-dimethylaminopentyl)spiro[chroman-4,4'-imidazolidine]-2',5'-dione,
2,2-dimethyl-6-chloro-1'-(6-dimethylaminohexyl)spiro[chroman-4,4'-imidazolidine]-2',5'-dione,
2,2'-dimethyl-6-chloro-1'-(7-dimethylaminoheptyl)spiro[chroman-4,4'-imidazolidine]-2',5'-dione, 6-chloro-2-methyl-1'-(6-dimethylaminohexyl)spiro[chroman-4,4'-imidazolidine]-2',5'-dione, 2,2-dimethyl-6-fluoro-1'-(6-dimethylaminohexyl)spiro[chroman-4,4'-imidazolidine]-2',5'-dione, 2,2-dimethyl-6-fluoro-1'-(4-dimethylaminobutyl)spiro[chroman-4,4'-imidazolidine]-2',5'-dione, 2,2-dimethyl-6-fluoro-1'-(3-morpholinopropyl)spiro[chroman-4,4'-imidazolidine]-2',5'-dione, 2,2-dimethyl-6-fluoro-1'-[(3-hydroxyamino)propyl]-spiro[chroman-4,4'-imidazolidine]-2',5'-dione, 2,2-dimethyl-6-fluoro-1'-{3-[bis(2-hydroxyethyl)amino]propyl}spiro[chroman-4,4'-imidazolidine]-2',5'-dione, 6-chloro-1'-(3-dimethylaminopropyl)spiro[chroman-4,4'-imidazolidine]-2',5'-dione, 8-chloro-1'-(3-dimethylaminopropyl)spiro[chroman-4,4'-imidazolidine]-2',5'-dione, 2,5-dimethyl-6-fluoro-1'-(2-dimethylaminoethyl)spiro[chroman-4,4'-imidazolidine]-2',5'-dione, 1-(3-dimethylaminopropyl)spiro[chroman-4,4'-imidazolidine]-2',5'-dione, 2,2-dimethyl-6-fluoro-1'-{3-[2-(3,4-dimethoxyphenyl)ethylmethylamino]propyl}spiro[chroman-4,4'-imidazolidine]-2',5'-dione, 2,2-dimethyl-6-fluoro-1'-{3-[4-(2-methoxyphenyl)piperazinol]propyl}spiro[chroman-4,4'-imidazolidine]-2',5'-dione, 2,2-dimethyl-6-bromo-1'-(6-dimethylaminohexyl)spiro[chroman-4,4'-imidazolidine]-2',5'-dione, 2,2-dimethyl-6-bromo-1'-(4-dimethylaminobutyl)spiro[chroman-4,4'-imidazolidine]-2',5'-dione, 2,2-dimethyl-6-methyl-1'-(3-dimethylaminopropyl)-spiro[chroman-4,4'-imidazolidine]-2',5'-dione, 2,2-dimethyl-6-methoxy-1'-(3-dimethylaminopropyl)-spiro[chroman-4,4'-imidazolidine]-2',5'-dione, 2,2-dimethyl-6-nitro-1'-(3-dimethylaminopropyl)spiro[chroman-4,4'-imidazolidine]-2',5'-dione, 2,2-di-n-butyl-6-chloro-1'-(3-dimethylaminopropyl)-spiro[chroman-4,4'-imidazolidine]-2',5'-dione, 2,2-di-n-hexyl-6-chloro-1'-(3-dimethylaminopropyl)-spiro[chroman-4,4'-imidazolidine]-2',5'-dione, 6-chloro-2-n-hexyl-1'-(3-dimethylaminopropyl)spiro[chroman-4,4'-imidazolidine]-2',5'-dione.

2.2-dimethyl-6-nitro-1'-[3-(4-hydroxypiperidino)propyl]spiro[chroman-4,4'-imidazolidine]-2',5-dione, 2.2-dimethyl-6.8-dinitro-1'-[3-(4-hydroxypiperridino)propyl]spiro[chroman-4,4'-imidazolidine]-2',5'-dione 2.2-dimethyl-6-fluoromethyl-1'-[3-(4-hydroxypiperidino)propyl]spiro[chroman-4,4'-imidazolidine]-2',5'-dione 2.2-dimethyl-6-chloro-1'[3-(4-octanoyloxypiperidino)propyl]spiro[chroman-4,4'-imidazolidine]-2',5'-dione 2.2-dimethyl-$\beta,\beta,\beta$-trifluorolthoxy-1'-[3-(4-hydroxypiperidino)propyl]spiro[chroman-4,4'-imidazolidine]-2',5'-dione 2.2-dimethyl-6-chroro-1'-(3-benzylaminopropyl)-spiro[chroman-4,4'-imidazolidine]-2',5'-dione 2.2-dimethyl-6-chroro-1'-[3-(4-methylpiperidino)propyl]-spiro[chroman-4,4'-imidazolidine]-2',5'-dione The compounds of the formula (1) of the present invention and their salts are new compounds which have not been disclosed in literature as far as we are aware yet. They have an excellent antiarrhythmic activity with only a low toxicity. They are useful as antiarrhythmic agents for the treatment of arrhythmia of various types.

The compounds of the present invention have a chemical structural formula (I) shown above which is utterly different from those of known antiarrhythmic agents and is quite unique.

The compounds of the present invention have a characteristic feature that they have no cardioinhibitory effect. This is quite advantageous when they are used as the antiarrhythmic agents.

The antiarrhythmic activity of the compounds of the present invention lasts for a long time. The compounds have only a low toxicity and a wide safety margin (high therapeutic index). Therefore, the compounds are useful as preferred antiarrhythmic agents.

The results of the following pharmacological tests will prove the effects of the compounds of the present invention.

EXPERIMENTAL EXAMPLE (1) Chloroform-induced arrhythmia (mice):

Ventricular arrhythmia was caused experimentally in mice by the following method.

The mice were placed in a device filled with chloroform gas. After expiring, the ventricular pulse was counted from a record of an electrocardiogram. The antiarrhythmic activity of the test compound was determined based on its effect of relieving tachycardia. The lethal dose, toxic dose and minimum effective dose of each compound were determined. The compounds were tested by administration by two routes, i.e. peroral and intravenous injection. Relative peroral effects of them were inferred from the results. The lasting time (duration) was inferred from changes in the medicinal effects observed when the time interval between the administration of the compound and the treatment of the mice with chloroform was varied. Table 1 shows the results (effective dose on arrhythmia and lethal dose) of experiments wherein a test compound was given to mice perorally one hour before the treatment with chloroform. As comparative standard medicines, quinidine, disopyramide and phenytoin were employed. This method is taught in the publication, J. Pharmacol. Exp. Ther. 160,22 (1968), by J. W. Lawson.

TABLE 1

$$\text{structure: benzene ring (positions 5,6,7,8) fused with oxygen-containing ring (positions 1,2,3,4); position 5 has HN-OC-; position 4 has -CO-N(-(CH_2)_n-Z); position 2 has R^1, R^2; position 6 has X^1; position 8 has X^2}$$

| Test compound | | | | | | Effective dose | Lethal dose |
|---|---|---|---|---|---|---|---|
| $X^1$ | $X^2$ | $R^1$ | $R^2$ | n | Z | (mg/kg) | (mg/kg) |
| 6-F | H | $CH_3$ | $CH_3$ | 2 | $-N(C_2H_5)_2$ | 12.5 | 200 |
| 6-F | H | $CH_3$ | $CH_3$ | 2 | $-N(i-C_3H_7)_2$ | 25 | 200 |
| 6-F | H | $CH_3$ | $CH_3$ | 2 | $-N(CH_3)_2$ | 50 | 400 |
| 6-Cl | H | H | $CH_3$ | 3 | $-N(CH_3)_2$ | 12.5 | 50 |
| 6-Cl | H | $C_2H_5$ | $C_2H_5$ | 3 | $-N(CH_3)_2$ | 25 | 400 |
| 6-Cl | H | $CH_3$ | $CH_3$ | 3 | -N(piperidinyl)-OH | 25 | 400 |
| 6-F | H | $CH_3$ | $CH_3$ | 3 | -N(piperidinyl)-OH | 25 | 400 |
| 6-Cl | 8-Cl | $CH_3$ | $CH_3$ | 3 | -N(piperidinyl)-OH | 12.5 | 400 |
| 6-F | H | $CH_3$ | $CH_3$ | 3 | -N(piperidinyl)-phenyl | 50 | 200 |
| 6-F | H | $C_2H_5$ | $C_2H_5$ | 3 | -N(piperidinyl)-OH | 25 | 400 |
| 6-F | H | $CH_3$ | $CH_3$ | 3 | -N(piperidinyl)-$OCH_3$ | 25 | 400 |
| | | | Quinidine sulfonate | | | 200 | 800 |
| | | | Disopyramide phosphate | | | 50 | 600 |
| | | | Phenytoin sodium | | | 100 | >800 |

It is apparent from Table 1 that the antiarrhythmic activities of the compounds of the present invention are stronger than those of the comparative ones and the safety margin (ratio of the lethal dose to the effective dose) of the former is larger than that of the latter.

The effects of these compounds lasted for 3 to 6 h after the peroral administration.

(2) Aconitine-induced arrhythmia (mice):

A toxic dose of aconitine was administered to mice and a ventricular extrasystole caused thereby was examined. When 0.1 mg/kg of aconitine is given to mice by intraabdominal injection, the ventricular tachycardia is caused in 20 min in general. In this experiment, a test compound in given doses as in the above experiment (1) was given to the mice perorally and, after a given time, aconitine was administered by injection. The occurrence of arrhythmia was examined and the ventricular extrasystole was counted from the electrocardiogram to determine the antiarrhythmic activity. Table 2 shows the results of the tests in which a test compound or a comparative standard medicine (quinidine or disopyramide) was administered perorally one hour before the intraabdominal injection of 0.1 mg/kg of aconitine. This method is taught in the publication, IUPHAR 9th International Congress of Pharmacology (Abstacts 454p) by T. Igarashi.

TABLE 2

(A) Structure showing OC—N—(CH$_2$)$_n$—N—piperidine-OH, with HN, CO, Cl-substituted chroman, and CH$_3$, CH$_3$ groups.

(B) Structure showing OC—N—(CH$_2$)$_3$—N—piperidine-OH, with HN, CO, X$^1$ and X$^2$ substituents on chroman with positions 5,6,7,8 and 2,3,4, and CH$_3$, CH$_3$ groups.

| Test compound | Effective dose (mg/kg) |
|---|---|
| general formula (A) | |
| n = 2 | 80 |
| n = 3 | 5 |
| n = 4 | 10 |
| n = 5 | 40 |
| n = 6 | 40 |
| n = 7 | 40 |
| general formula (B) | |
| X$^1$ = 6-F, X$^2$ = H | 5 |
| X$^1$ = 6-Cl, X$^2$ = H | 5 |
| X$^1$ = 6-Br, X$^2$ = H | 10 |
| X$^1$ = 6-CH$_3$, X$^2$ = H | >80 |
| X$^1$ = 6-Cl, X$^2$ = 8-Cl | 10 |
| Quinidine sulfate | 80 |
| Disopyramide phosphate | 40 |

The effective dose shown in Table 2 is that required for treating the aconitine-induced ventricular tachycardia to realize a ratio of normal sinus rhythm to ventricular pulse of about 1:1. Many of the test compounds exhibited their effects in an amount smaller than that of quinidine or disopyramide.

When the compounds were used in an amount larger than the effective amount shown in Table 2, aconitine-induced ventricular arrhythmia was normalized to recover the perfect sinus rhythm. This effect lasted even 6 hours after the peroral administration.

(3) Acute toxicity (rats):

The acute toxicity tests on rats (peroral administration) were effected using typical compounds of the present invention, i.e. 6-chloro-2,2-dimethyl-1'-[3-(4-hydroxypiperidino)propyl]spiro[chroman-4,4'-imidazolidine]-2',5'-dione (compound 1) and 2,2-dimethyl-6-fluoro-1'-[3-(4-hydroxypiperidino)propyl]-spiro[chroman-4,4'-imidazolidine]-2',5'-dione (compound 2). The results are shown in Table 3.

TABLE 3

| | LD$_{50}$ | mg/kg |
|---|---|---|
| Compound 1 | ♂ | 930 |
| | ♀ | 858 |
| Compound 2 | ♂ | 860 |
| | ♀ | 780 |

The results of the above-mentioned tests proved that the compounds of the present invention have an excellent, long-lasting antiarrhythmic activity, low toxicity and wide safety margin (high therapeutic index) and they can be used as preferred antiarrhythmic agents.

The antiarrhythmic mechanism of the compounds of the present invention was examined on the basis of the effects on resting potential and action potential of extracted myocardia of guinea pigs and swine by a microelectrode method. As a result, it was found that the compounds of the present invention reduce the rate of the action potential rise, although they exert no influence on the resting potential. Particularly when the electric stimulation was strong, the action potential-inhibiting effect was strong. This property is common to antiarrhythmic agents of Class 2 (quinidine, disopyramide). This fact indicates that the mechanism and diseases for which the compounds of the present invention are efficacious (i.e. supraventricular and ventricular arrhythmia) are the same as those of the antiarrhythmic agents of Class 2.

One of the pharmacological features of the compounds of the present invention is that they do not substantially inhibit the contraction of the myocardia. This property is quite preferred when they are used as antiarrhythmic agents. More particularly, although quinidine and disopyramide reduce the contraction power of the myocardia in a dose several times as much as that required for realizing the antiarrhythmic effects, the compounds of the present invention exhibit no influence on the contraction power of the myocardia even when administered in an amount 10 times as much as the effective dose for the antiarrhythmia treatment.

The compounds of the present invention are effective for the treatment and prevention of various types of arrhythmia such as ventricular arrhythmia and atrial (supraventricular) arrhythmia.

In using the compounds of the present invention as antiarrhythmic agents, they are administered perorally or parenterally (intramuscular, subcutaneous or intravenous administration). The dosage varies depending on the patient, symptoms and age and is not particularly limited. However, generally, the dosage is about 1 to 1,000 mg/day, preferably about 100 to 300 mg/day, for adult human beings.

The compounds of the present invention can be formulated into tablets, granules, powders, capsules, injections and suppositories by any methods generally employed in the pharmaceutical field.

In the preparation of peroral solid products, an excipient and, if necessary, binder, disintegrator, lubricant, colorant and corrigent are added to the active ingredient and the mixture is shaped into tablets, coated tablets, granules, powders or capsules by a conventional method.

The excipients include, for example, lactose, corn starch, white sugar, glucose, sorbitol and crystalline cellulose. The binders include, for example, polyvinyl alcohol, polyvinyl ether, ethylcellulose, methylcellulose, gum arabic, tragacanth, gelatin, shellac, hydroxypropylcellulose, hydroxypropylstarch and polyvinylpyrrolidone. The disintegrators include, for example, starch, agar, gelatin powder, crystalline cellulose, calcium carbonate, sodium hydrogencarbonate, calcium citrate, dextrin and pectin. The lubricants include, for example, magnesium stearate, talc, polyethylene glycol, silica and hardened vegetable oils. The colorants include, for example, those allowed for medicines. The corrigents include, for example, cocoa powder, menthol, aromatic powder, peppermint oil, borneol and cinnamon powder. These tablets and granules can be coated with sugar, gelatin or the like, if necessary.

In the formulation of the injections, necessary components such as a pH-adjusting agent, buffering agent, stabilizer, solubilizer and preservative are added to the active ingredient and the mixture is formulated into subcutaneous, intramuscular or intravenous injectable solutions by a conventional method.

The following examples will further illustrate the present invention, but these examples by no means limit the scope of the invention.

EXAMPLE 1

2,2-Dimethyl-6-fluoro-1'-[3-(4-hydroxypiperidino)propyl]spiro[chroman-4,4'-imidazolidine]-2',5'-dione (1) 2,2-Dimethyl-6-fluoro-1'-(3-bromopropyl)spiro[chroman-4,4'-imidazolidine]-2',5'-dione:

1.0 g (25 mM) of sodium hydride (60% suspension in mineral oil) was added to a solution of 6.6 g (25 mM) of 2,2-dimethyl-6-fluoro-spiro[chroman-4,4'-imidazolidine]-2',5'-dione and a solution of 10.1 g (50 mM) of 1,3-dibromopropane in 70 ml of dimethylformamide at 15° to 30° C. The mixture was stirred at room temperature for 5 h. The reaction liquid was poured into ice/water. After extraction with ethyl acetate, the resulting ethyl acetate layer was washed with water and then dried over magnesium sulfate. The solvent was distilled off under reduced pressure. 12.7 g of a residue was purified according to silica gel column chromatography (developer: dichloromethane/ethanol) to obtain 6.95 g (yield: 72.2%) of the intended compound.

melting point: 190° to 192° C.

| elementary analysis for $C_{16}H_{18}BrFN_2O_3$: | | | |
|---|---|---|---|
| | C | H | N |
| calculated (%) | 49.87 | 4.71 | 7.27 |
| found (%) | 49.63 | 4.59 | 7.15 |

NMR (CDCl$_3$): 1.32 (3H, s), 1.50 (3H, s), 2.02 (1H, d, J=16 Hz), 2.24 (2H, q, J=8 Hz), 2.60 (1H, d, J=16Hz), 3.40 (2H, t, J=8 Hz), 3.74 (2H, t, J=8 Hz), 6.36 (1H, s), 6.45–7.10 (3H, m)

(2) 2,2-Dimethyl-6-fluoro-1'-[3-(4-hydroxypiperidino)propyl]spiro[chroman-4,4'-imidazolidine]-2',5'-dione:

6.0 g (15.6 mM) of the bromine compound obtained in the above step (1) of Example (1), 3.15 g (31.2 mM) of 4-hydroxypiperidine, 4.31 g (31.2 mM) of potassium carbonate and a solution of a small amount of potassium iodide in 70 ml of dimethylformamide were reacted together at 80° C. for 5 h. The reaction liquid was poured into water and extracted with ethyl acetate. The resulting ethyl acetate layer was washed with water and then dried over magnesium sulfate. The solvent was distilled off under reduced pressure and the residue was recrystallized from ethanol/ethyl acetate to obtain 5.85 g (yield: 92.6%) of the intended compound. The product was then converted into its hydrochloride salt by a conventional method.

melting point: 211° to 213° C. (free form): 195° to 197° C. (hydrochloride).

| elementary analysis for $C_{21}H_{38}FN_3O_4$: | | | |
|---|---|---|---|
| | C | H | N |
| calculated (%) | 62.20 | 6.96 | 10.36 |
| found (%) | 61.92 | 7.01 | 10.25 |

NMR (CDOD)$\delta$: 1.32 (3H, s), 1.52 (3H, s), 1.60–3.00 (14H, m), 3.62 (2H, t, J=8 Hz), 3.45–3.80 (1H, m), 6.50–7.10 (3H, m)

EXAMPLE 2

8-Chloro-1'-(3-dimethylaminopropyl)spiro[chroman-4,4'-imidazolidine]-2',5'-dione 240 mg (6 mM) of sodium hydride (60% suspension in mineral oil) was added to a solution of 1.52 g (6 mM) of 8-chloro-spiro[chroman-4,4'-imidazolidine]-2',5'-dione in 30 ml of dimethylformamide at 5° C. The mixture was stirred for 10 min. Then, a solution of 802 mg (6.6 mM) of 3-dimethylaminopropyl chloride in 3 ml of dimethylformamide was added dropwise thereto at room temperature over 10 min. The reaction was carried out at 80° to 90° C. for 5 h. The reaction liquid was poured into ice/water and extracted with ethyl acetate. The resulting ethyl acetate layer was washed with water and then dried over magnesium sulfate. The solvent was distilled under reduced pressure. 2.65 g of a residue was purified according to silica gel column chromatography (developer: dichlorometane/ethanol) to obtain 1.60 g (yield: 79.0%) of the intended compound. The product was then converted into its hydrochloride by a conventional method.

melting point: 158° to 159° C. (free form); 202° to 204° C. (HCl salt).

| elementary analysis for $C_{16}H_{20}ClN_3O_3C$ | | | |
|---|---|---|---|
| | C | H | N |
| calculated (%): | 56.89 | 5.97 | 12.44 |
| found (%) | 56.84 | 5.93 | 12.39 |

NMR (CDCl$_3$)$\delta$: 1.60–1.96 (2H, m), 2.14 (6H, s), 2.00–2.44 (4H, m), 3.58 (2H, t, J=8 Hz), 4.18–4.44 (1H, m), 4.64–4.98 (1H, m), 6.16 (1H, s), 6.60–7.02 (2H, m), 7.16–7.36 (1H, m)

EXAMPLES 3 to 84

(1) Intermediates shown in the following Tables 4 and 5 were obtained in the same manner as in Example 1-(1).

(2) The intended compounds shown in the following Tables 6, 7, 8 and 9 were obtained in the same way as in Example 1-(2) or Example 2.

TABLE 4

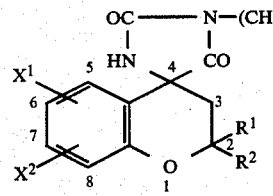

| X¹ | X² | R¹ | R² | n | m.p. (°C.) | C (%) | H (%) | N (%) |
|---|---|---|---|---|---|---|---|---|
| 6-F | H | CH₃ | CH₃ | 4 | 144–146 | 51.14 | 5.05 | 7.02 |
|  |  |  |  |  |  | 51.38 | 5.16 | 7.01 |
| 6-Cl | H | CH₃ | CH₃ | 3 | 191–194 | 47.84 | 4.52 | 6.97 |
|  |  |  |  |  |  | 48.10 | 4.53 | 7.02 |
| 7-OCH₃ | 8-CH₃ | CH₃ | CH₃ | 3 | 211–213 | 52.56 | 5.64 | 6.81 |
|  |  |  |  |  |  | 52.27 | 5.60 | 6.54 |
| 6-Cl | H | H | H | 3 | 181–183 | 45.01 | 3.78 | 7.50 |
|  |  |  |  |  |  | 45.26 | 3.80 | 7.62 |
| 6-Cl | H | C₂H₅ | C₂H₅ | 3 | 172–174 | 50.31 | 5.16 | 6.52 |
|  |  |  |  |  |  | 50.47 | 5.15 | 6.45 |
| 6-F | H | CH₃ | CH₃ | 2 | 201–203 | 48.54 | 4.35 | 7.55 |
|  |  |  |  |  |  | 48.73 | 4.37 | 7.51 |
| 6-F | H | CH₃ | CH₃ | 6 | 97.5–99.5 | 53.40 | 5.66 | 6.55 |
|  |  |  |  |  |  | 53.42 | 5.67 | 6.52 |
| 6-Cl | H | CH₃ | CH₃ | 4 | 183–186 | 49.12 | 4.85 | 6.74 |
|  |  |  |  |  |  | 49.37 | 4.89 | 6.57 |
| 6-Cl | H | CH₃ | CH₃ | 5 | 181–184 | 50.31 | 5.16 | 6.52 |
|  |  |  |  |  |  | 50.19 | 5.17 | 6.48 |
| 6-Cl | H | CH₃ | CH₃ | 6 | 120.5–122 | 51.42 | 5.45 | 6.31 |
|  |  |  |  |  |  | 51.37 | 5.37 | 6.39 |
| 6-Cl | H | CH₃ | CH₃ | 7 | 125–126 | 52.47 | 5.73 | 6.12 |
|  |  |  |  |  |  | 52.57 | 5.81 | 6.07 |
| 6-Cl | H | C₂H₅ | C₂H₅ | 3 | 171–173 | 50.31 | 5.16 | 6.52 |
|  |  |  |  |  |  | 50.27 | 5.08 | 6.51 |

TABLE 5

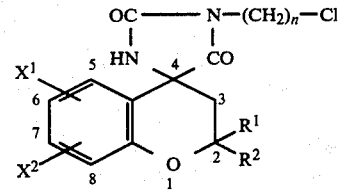

| X¹ | X² | R¹ | R² | n | m.p. (°C.) | C(%) | H(%) | N(%) |
|---|---|---|---|---|---|---|---|---|
| 6-Cl | H | CH₃ | H | 3 | 146–148 | 52.50 | 4.70 | 8.16 |
|  |  |  |  |  |  | 52.65 | 4.77 | 8.08 |
| 6-F | H | CH₃ | H | 3 | 143–145 | 55.14 | 4.94 | 8.57 |
|  |  |  |  |  |  | 55.32 | 4.98 | 8.43 |
| 6-Cl | H | CH₃ | CH₃ | 3 | 204–206 | 53.80 | 5.08 | 7.84 |
|  |  |  |  |  |  | 53.93 | 5.12 | 7.73 |

TABLE 6

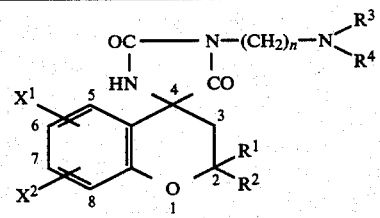

| Example | X¹ | X² | R¹ | R² | n | R³ | R⁴ | m.p. (°C.) | Molecular formula | C (%) | H (%) | N (%) |
|---|---|---|---|---|---|---|---|---|---|---|---|---|
| 3 | 6-Cl | H | H | CH₃ | 2 | CH₃ | CH₃ | 300 | C₁₆H₂₀ClN₃O₃.HCl | 51.34 | 5.65 | 11.23 |
|  |  |  |  |  |  |  |  |  |  | 51.52 | 5.77 | 11.35 |
| 4 | 6-Cl | H | H | CH₃ | 3 | CH₃ | CH₃ | 300 | C₁₇H₂₂ClN₃O₃.HCl | 52.58 | 5.97 | 10.82 |
|  |  |  |  |  |  |  |  |  |  | 52.37 | 5.98 | 10.75 |
| 5 | 6-F | H | H | CH₃ | 2 | CH₃ | CH₃ | 300 | C₁₆H₂₀FN₃O₃.HCl | 51.34 | 5.65 | 11.23 |
|  |  |  |  |  |  |  |  |  |  | 51.57 | 5.56 | 11.34 |
| 6 | 6-Cl | H | H | CH₃ | 2 | C₂H₅ | C₂H₅ | 270–272 | C₁₈H₂₄ClN₃O₃.HCl | 53.73 | 6.26 | 10.44 |
|  |  |  |  |  |  |  |  |  |  | 53.88 | 6.13 | 10.45 |
| 7 | 6-Cl | H | CH₃ | CH₃ | 3 | CH₃ | CH₃ | 269–270 | C₁₈H₂₄ClN₃O₃.HCl | 53.73 | 6.26 | 10.44 |
|  |  |  |  |  |  |  |  |  |  | 53.84 | 6.19 | 10.35 |
| 8 | 6-Cl | H | H | C₂H₅ | 3 | CH₃ | CH₃ | 262–263 | C₁₈H₂₄ClN₃O₃.HCl | 53.73 | 6.26 | 10.44 |
|  |  |  |  |  |  |  |  |  |  | 53.89 | 6.20 | 10.47 |
| 9 | 6-Cl | H |  |  | 3 | CH₃ | CH₃ | 230–241 | C₂₁H₂₈ClN₃O₃.HCl | 57.01 | 6.38 | 9.50 |
|  |  |  |  |  |  |  |  |  |  | 58.95 | 6.27 | 9.61 |

TABLE 6-continued

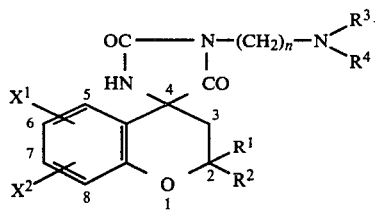

| Example | $X^1$ | $X^2$ | $R^1$ | $R^2$ | n | $R^3$ | $R^4$ | m.p. (°C.) | Molecular formula | C (%) | H (%) | N (%) |
|---|---|---|---|---|---|---|---|---|---|---|---|---|
| 10 | 6-Br | H | $CH_3$ | $CH_3$ | 3 | $CH_3$ | $CH_3$ | 277–279 | $C_{18}H_{24}BrN_3O_3 \cdot HCl$ | 48.50 / 48.29 | 5.65 / 5.73 | 9.43 / 9.21 |
| 11 | 6-Cl | H | ⌐⌐ | $CH_3$ | 3 | $CH_3$ | | waxy | $C_{20}H_{26}ClN_3O_3 \cdot HCl$ | 56.08 / 56.02 | 6.12 / 6.17 | 9.81 / 9.75 |
| 12 | 6-F | 8-$NO_2$ | $CH_3$ | $CH_3$ | 3 | $CH_3$ | $CH_3$ | 274–276 | $C_{18}H_{23}FN_4O_5 \cdot HCl$ | 52.11 / 52.24 | 5.83 / 5.75 | 13.51 / 13.59 |
| 13 | 6-F | H | $CH_3$ | $CH_3$ | 3 | $CH_3$ | $CH_3$ | 146–169 | $C_{18}H_{24}FN_3O_3 \cdot HCl$ | 56.17 / 56.23 | 6.55 / 6.51 | 10.92 / 10.75 |
| 14 | 6-Cl | H | $C_2H_5$ | $C_2H_5$ | 3 | $CH_3$ | $CH_3$ | 203–205 | $C_{20}H_{28}ClN_3O_3 \cdot HCl$ | 60.98 / 60.73 | 7.16 / 7.08 | 10.67 / 10.62 |
| 15 | 6-F | H | H | $CH_3$ | 3 | $CH_3$ | $CH_3$ | waxy | $C_{17}H_{22}FN_3O_3 \cdot HCl$ | 54.91 / 54.78 | 6.23 / 6.15 | 11.30 / 11.21 |
| 16 | 6-F | H | $CH_3$ | $CH_3$ | 2 | $C_2H_5$ | $C_2H_5$ | 154–156 | $C_{19}H_{20}FN_3O_3$ | 62.79 / 62.74 | 7.21 / 7.28 | 11.56 / 11.49 |
| 17 | 6-F | H | $CH_3$ | $CH_3$ | 2 | $C_2H_5$ | $C_2H_5$ | 206–208 | $C_{19}H_{20}FN_3O_3 \cdot HCl$ | 57.07 / 56.98 | 6.81 / 6.95 | 10.51 / 10.35 |
| 18 | 6-F | H | $CH_3$ | $CH_3$ | 2 | i-$C_3H_7$ | i-$C_3H_7$ | 122–124 | $C_{21}H_{30}FN_3O_3$ | 64.43 / 64.43 | 7.72 / 7.82 | 10.73 / 10.67 |
| 19 | 6-F | H | $CH_3$ | $CH_3$ | 2 | i-$C_3H_7$ | i-$C_3H_7$ | 230–233 | $C_{21}H_{30}FN_3O_3 \cdot HCl$ | 58.94 / 58.75 | 7.30 / 7.25 | 9.82 / 9.60 |
| 20 | 6-F | H | $CH_3$ | $CH_3$ | 3 | $C_2H_5$ | $C_2H_5$ | 99–100 | $C_{20}H_{28}FN_3O_3$ | 63.64 / 63.54 | 7.48 / 7.54 | 11.13 / 11.02 |
| 21 | 6-F | H | $CH_3$ | $CH_3$ | 3 | $C_2H_5$ | $C_2H_5$ | 232–235 | $C_{20}H_{28}FN_3O_3 \cdot HCl$ | 58.03 / 57.82 | 6.82 / 7.11 | 10.15 / 9.95 |
| 22 | 6-F | H | $CH_3$ | $CH_3$ | 3 | n-$C_3H_7$ | n-$C_3H_7$ | 235–237 | $C_{22}H_{32}FN_3O_3 \cdot HCl$ | 59.79 / 59.57 | 7.30 / 7.25 | 9.51 / 9.27 |
| 23 | 6-F | H | $CH_3$ | $CH_3$ | 3 | morpholino | | 235–238 | $C_{20}H_{26}FN_3O_4 \cdot HCl$ | 56.14 / 55.94 | 6.13 / 6.40 | 9.82 / 9.54 |
| 24 | 6-F | H | $CH_3$ | $CH_3$ | 3 | H | $(CH_2)_3OH$ | 138–139 | $C_{19}H_{26}FN_3O_4$ | 60.14 / 59.87 | 6.91 / 6.85 | 11.07 / 10.91 |
| 25 | 6-F | H | $CH_3$ | $CH_3$ | 3 | H | $(CH_2)_3OH$ | 187–189 | $C_{19}H_{26}FN_3O_4 \cdot HCl$ | 54.61 / 54.41 | 6.75 / 6.52 | 10.05 / 9.82 |
| 26 | 6-F | H | $CH_3$ | $CH_3$ | 3 | $(CH_2)_3OH$ | $(CH_2)_3OH$ | 198–200 | $C_{20}H_{30}FN_3O_5 \cdot HCl$ | 55.61 / 55.41 | 7.00 / 6.78 | 9.73 / 9.65 |
| 27 | 6-Cl | H | H | H | 3 | $CH_3$ | $CH_3$ | 131–133 | $C_{16}H_{20}ClN_3O_3$ | 56.89 / 56.78 | 5.97 / 5.82 | 12.44 / 12.65 |
| 28 | 6-Cl | H | H | H | 3 | $CH_3$ | $CH_3$ | 279–281 | $C_{16}H_{20}ClN_3O_3 \cdot HCl$ | 51.35 / 51.33 | 5.66 / 5.64 | 11.23 / 11.17 |
| 29 | 8-Cl | H | H | H | 3 | $CH_3$ | $CH_3$ | 158–159 | $C_{16}H_{20}ClN_3O_3$ | 56.89 / 56.84 | 5.97 / 5.93 | 12.44 / 12.39 |
| 30 | 8-Cl | H | H | H | 3 | $CH_3$ | $CH_3$ | 202–203 | $C_{16}H_{20}ClN_3O_3 \cdot HCl$ | 51.35 / 51.33 | 5.66 / 5.57 | 11.23 / 11.37 |
| 31 | 6-F | H | $CH_3$ | $CH_3$ | 2 | $CH_3$ | $CH_3$ | 234–235 | $C_{17}H_{22}FN_3O_3 \cdot HCl$ | 54.91 / 54.75 | 6.23 / 6.11 | 11.30 / 11.21 |
| 32 | H | H | H | H | 3 | $CH_3$ | $CH_3$ | 118–120 | $C_{16}H_{21}N_3O_3$ | 63.35 / 63.31 | 6.98 / 6.91 | 13.85 / 13.81 |
| 33 | 6-F | H | $CH_3$ | $CH_3$ | 3 | $CH_3$ | $(CH_2)_2$-C$_6H_3$(OCH$_3$)$_2$ | waxy | $C_{27}H_{24}FN_3O_3 \cdot HCl$ | 60.49 / 60.51 | 6.39 / 6.27 | 7.84 / 7.78 |

TABLE 6-continued

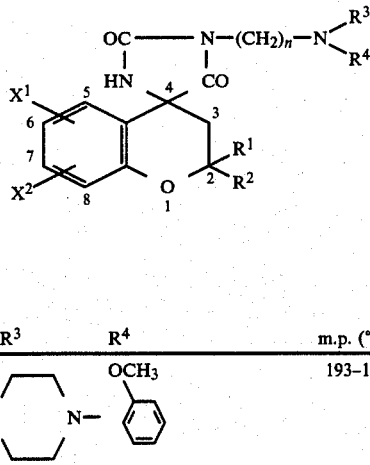

| Example | X¹ | X² | R¹ | R² | n | R³ | R⁴ | m.p. (°C.) | Molecular formula | C (%) | H (%) | N (%) |
|---|---|---|---|---|---|---|---|---|---|---|---|---|
| 34 | 6-F | H | $CH_3$ | $CH_3$ | 3 | (piperidine N—) | $OCH_3$-phenyl | 193–197 | $C_{27}H_{33}FN_4O_4 \cdot HCl$ | 60.84 / 60.75 | 6.43 / 6.35 | 10.51 / 10.37 |
| 35 | H | H | $CH_3$ | $CH_3$ | 3 | $CH_3$ | $CH_3$ | 135–137 | $C_{18}H_{25}N_3O_3$ | 65.23 / 65.31 | 7.60 / 7.61 | 12.68 / 12.70 |
| 36 | 6-Cl | H | n-$C_3H_7$ | n-$C_3H_7$ | 3 | $CH_3$ | $CH_3$ | 112–115 | $C_{22}H_{32}ClN_3O_3 \cdot HCl$ | 57.64 / 57.59 | 7.26 / 7.31 | 9.17 / 9.25 |

TABLE 7

| Example | X¹ | X² | R¹ | R² | n | R⁵ | R⁶ | m.p. (°C.) | Molecular formula | C (%) | H (%) | N (%) |
|---|---|---|---|---|---|---|---|---|---|---|---|---|
| 37 | 6-Cl | H | H | $CH_3$ | 3 | phenyl | H | 219–221 | $C_{26}H_{30}ClN_3O_3 \cdot HCl$ | 61.29 / 61.39 | 6.09 / 6.21 | 8.20 / 8.30 |
| 38 | 6-Cl | H | H | $CH_3$ | 3 | phenyl | OH | 186–188 | $C_{26}H_{30}ClN_3O_4 \cdot HCl$ | 58.97 / 58.63 | 6.09 / 5.86 | 7.93 / 7.93 |
| 39 | 6-F | H | H | $CH_3$ | 3 | phenyl | H | 196–198 | $C_{26}H_{30}FN_3O_3$ | 61.71 / 61.57 | 6.37 / 6.38 | 8.30 / 8.31 |
| 40 | 6-F | H | H | H | 3 | phenyl | H | 175–177 | $C_{25}H_{28}FN_3O_3$ | 62.16 / 62.39 | 6.26 / 6.29 | 8.70 / 8.57 |
| 41 | 6-Cl | H | $CH_3$ | $CH_3$ | 3 | phenyl | H | 215–217 | $C_{27}H_{32}ClN_3O_3 \cdot HCl$ | 62.54 | 6.41 | 8.10 |
| 42 | 6-Cl | H | $CH_3$ | $CH_3$ | 3 | phenyl | OH | 227–229 | $C_{27}H_{32}ClN_3O_4 \cdot HCl$ | 60.67 / 60.42 | 6.22 / 6.18 | 7.86 / 7.91 |

TABLE 7-continued

| Example | $X^1$ | $X^2$ | $R^1$ | $R^2$ | n | $R^5$ | $R^6$ | m.p.(°C.) | Molecular formula | C (%) | H (%) | N (%) |
|---|---|---|---|---|---|---|---|---|---|---|---|---|
| 43 | 6-CH₃ | H | H | CH₃ | 3 |  | H | 170–172 | $C_{27}H_{33}N_3O_3$ .HCl | 66.99 66.79 | 7.08 7.32 | 8.51 8.51 |
| 44 | 6-OCH₃ | H | H | CH₃ | 3 |  | H | 216–219 | $C_{27}H_{33}N_3O_4$.HCl | 64.85 64.70 | 6.65 6.69 | 8.40 8.34 |
| 45 | 6-Cl | 8-Cl | CH₃ | CH₃ | 3 | OH | H | waxy | $C_{21}H_{27}Cl_2N_3O_4$.HCl | 51.18 50.95 | 5.52 5.47 | 8.53 8.29 |
| 46 | 6-F | H | C₂H₅ | C₂H₅ | 3 | OH | H | waxy | $C_{23}H_{32}FN_3O_4$.HCl | 58.78 58.59 | 7.08 7.16 | 8.94 8.88 |
| 47 | 6-F | H | H | H | 3 | OH | H | 204–206 | $C_{19}H_{24}FN_3O_4$ | 60.46 60.19 | 6.40 6.45 | 11.13 11.01 |
| 48 | 6-CH₃ | H | CH₃ | CH₃ | 3 | OH | H | waxy | $C_{22}H_{31}N_3O_4$.HCl | 60.34 60.25 | 7.37 7.41 | 9.59 9.62 |
| 49 | 6-F | H | CH₃ | CH₃ | 3 | OH | H | 211–213 | $C_{21}H_{28}FN_3O_4$ | 62.20 61.92 | 6.96 7.01 | 10.36 10.25 |
| 50 | 6-F | H | CH₃ | CH₃ | 3 | OH | H | 195–197 | $C_{21}H_{28}FN_3O_4$.HCl | 57.07 56.77 | 6.61 6.67 | 9.51 9.24 |
| 51 | 6-F | H | CH₃ | CH₃ | 3 | OCH₃ | H | 207–208 | $C_{22}H_{30}FN_3O_4$.HCl | 57.96 57.72 | 6.63 6.78 | 9.22 9.11 |
| 52 | 6-Cl | H | CH₃ | CH₃ | 3 | OH | H | 154–156 | $C_{21}H_{28}ClN_3O_4$ | 59.78 59.77 | 6.69 6.42 | 9.96 9.89 |
| 53 | 6-Cl | H | CH₃ | CH₃ | 3 | OH | H | 158–160 | $C_{21}H_{28}ClN_3O_4$.HCl | 55.03 55.01 | 6.38 6.57 | 9.17 9.15 |
| 54 | 7-OCH₃ | 8-CH₃ | CH₃ | CH₃ | 3 | OH | H | 156–158 | $C_{23}H_{33}N_3O_5$ | 64.01 63.98 | 7.71 7.59 | 9.74 9.80 |
| 55 | 7-OCH₃ | 8-CH₃ | CH₃ | CH₃ | 3 | OH | H | 157–159 | $C_{23}H_{33}N_3O_5$.HCl | 59.03 58.93 | 7.32 7.04 | 8.99 8.85 |
| 56 | 6-Cl | H | H | H | 3 | OH | H | 219–221 | $C_{19}H_{24}ClN_3O_4$ | 57.94 57.67 | 6.14 6.12 | 10.67 10.60 |
| 57 | 6-Cl | H | H | H | 3 | OH | H | 255–258 | $C_{19}H_{24}ClN_3O_4$.HCl | 53.03 53.14 | 5.86 5.62 | 9.76 9.76 |
| 58 | 6-Cl | H | C₂H₅ | C₂H₅ | 4 | OH | H | 177–179 | $C_{23}H_{32}ClN_3O_4$ | 61.40 61.25 | 7.17 7.11 | 9.34 9.37 |
| 59 | 6-F | H | CH₃ | CH₃ | 4 | OH | H | 186–187 | $C_{22}H_{30}FN_3O_4$.HCl | 57.96 57.77 | 6.85 6.84 | 9.22 9.06 |
| 60 | 6-F | H | CH₃ | CH₃ | 3 | =O | | 154–156 | $C_{21}H_{26}FN_3O_4$ | 62.52 62.37 | 6.50 6.46 | 10.42 10.32 |
| 61 | 6-F | H | CH₃ | CH₃ | 3 | =O | | 153–155 | $C_{21}H_{26}FN_3O_4$.HCl | 57.34 57.25 | 6.19 6.02 | 9.55 9.37 |
| 62 | 6-F | H | CH₃ | CH₃ | 3 | —OCOCH₃ | H | 216–219 | $C_{23}H_{30}FN_3O_5$.HCl | 57.08 56.90 | 6.46 6.27 | 9.68 8.63 |
| 63 | 6-F | H | CH₃ | CH₃ | 3 | 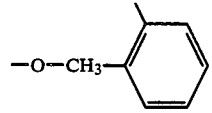 | OH | 169–172 | $C_{27}H_{32}FN_3O_4$.HCl | 62.60 62.57 | 6.42 6.51 | 8.11 8.23 |
| 64 | 8-Cl | H | H | H | 3 | OH | H | 144–146 | $C_{19}H_{24}ClN_3O_4$ | 57.94 57.71 | 6.14 6.08 | 10.67 10.51 |
| 65 | 8-Cl | H | H | H | 3 | OH | H | 274–276 | $C_{19}H_{24}ClN_3O_4$.HCl | 53.03 52.94 | 5.86 5.62 | 9.76 9.63 |
| 66 | 6-F | H | CH₃ | CH₃ | 3 | (2-Cl, -O-CH₃ phenyl) | H | 158–160 | $C_{28}H_{32}ClFN_3O_4$.HCl | 59.37 59.24 | 6.05 6.08 | 7.42 7.24 |

TABLE 7-continued

[Structure: chroman with HN-CO-N(CH₂)ₙ-N-piperidine(R⁵,R⁶) substituent at position 4, R¹R² at position 2, X¹ at 6, X² at 7]

| Example | X¹ | X² | R¹ | R² | n | R⁵ | R⁶ | m.p.(°C.) | Molecular formula | C (%) | H (%) | N (%) |
|---|---|---|---|---|---|---|---|---|---|---|---|---|
| 67 | 6-F | H | CH₃ | CH₃ | 2 | OH | H | 169–170 | C₂₀H₂₆FN₃O₄ | 61.37 / 61.34 | 6.70 / 6.80 | 10.73 / 10.56 |
| 68 | H | H | H | H | 3 | OH | H | 150–152 | C₁₉H₂₅N₃O₄ | 63.49 / 63.53 | 7.01 / 7.15 | 11.69 / 11.66 |
| 69 | 6-F | H | CH₃ | CH₃ | 3 | H | H | 256–258 | C₂₁H₂₈FN₃O₃·HCl | 59.22 / 59.15 | 6.86 / 6.78 | 9.87 / 10.01 |
| 70 | 6-F | H | CH₃ | CH₃ | 3 | —O–CH₂–CH₂–O— (ethylenedioxy) | | 146–148 | C₂₃H₂₈FN₃O₅ | 61.73 / 61.57 | 6.76 / 6.91 | 9.39 / 9.27 |
| 71 | 6-F | H | CH₃ | CH₃ | 3 | phenyl | H | 132 | C₂₇H₃₂FN₃O₃ | 69.66 / 69.50 | 6.93 / 6.91 | 9.03 / 8.93 |
| 72 | 6-F | H | CH₃ | CH₃ | 6 | OH | H | 145–146.5 | C₂₄H₃₄FN₃O₄ | 64.41 / 64.21 | 7.66 / 7.73 | 9.39 / 9.34 |
| 73 | 6-Cl | H | CH₃ | CH₃ | 4 | OH | H | 87–89 | C₂₂H₃₀ClN₃O₄ | 60.61 / 60.57 | 6.94 / 6.75 | 9.64 / 9.58 |
| 74 | 6-Cl | H | C₂H₅ | C₂H₅ | 3 | OH | H | 174–177 | C₂₃H₃₂ClN₃O₄ | 61.39 / 61.29 | 7.17 / 7.22 | 9.34 / 9.26 |
| 75 | 6-Cl | H | CH₃ | CH₃ | 5 | OH | H | 136–139 | C₂₃H₃₂ClN₃O₄ | 61.39 / 61.25 | 7.17 / 7.27 | 9.34 / 9.35 |
| 76 | 6-Cl | H | CH₃ | CH₃ | 7 | OH | H | 122–124 | C₂₅H₃₆ClN₃O₄ | 62.81 / 62.88 | 7.59 / 7.61 | 8.79 / 8.90 |
| 77 | 6-Cl | H | CH₃ | CH₃ | 6 | OH | H | 131–134 | C₂₄H₃₄ClN₃O₄ | 62.13 / 62.18 | 7.39 / 7.28 | 9.06 / 9.01 |

TABLE 8

[Structure: chroman with HN-CO-N(CH₂)ₙ-NR³R⁴ substituent at position 4]

| Example | X¹ | X² | R¹ | R² | n | R³ | R⁴ | m.p. (°C.) | Molecular formula | C (%) | H (%) | N (%) |
|---|---|---|---|---|---|---|---|---|---|---|---|---|
| 78 | 6-Cl | H | CH₃ | CH₃ | 3 | —CH₂—phenyl | H | 129–131 | C₂₃H₂₆ClN₃O₃ | 64.56 / 64.35 | 6.12 / 6.33 | 9.82 / 9.71 |
| 79 | 6-Cl | H | CH₃ | CH₃ | 3 | piperidino | CH₃ | 173.5–175 | C₂₁H₂₉ClN₄O₃ | 59.92 / 59.90 | 6.94 / 6.90 | 13.31 / 13.21 |

TABLE 9

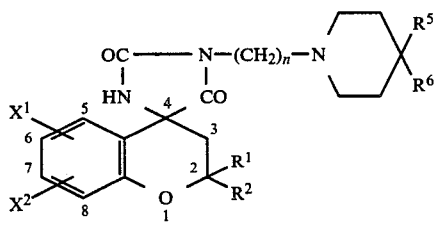

| Example | $X^1$ | $X^2$ | $R^1$ | $R^2$ | n | $R^5$ | $R^6$ | m.p. (°C.) | Molecular formula | C (%) | H (%) | N (%) |
|---|---|---|---|---|---|---|---|---|---|---|---|---|
| 80 | 6-$NO_2$ | H | $CH_3$ | $CH_3$ | 3 | OH | H | 173.5–175 | $C_{21}H_{28}N_4O_6$ | 58.32 / 58.02 | 6.53 / 6.53 | 12.96 / 12.96 |
| 81 | 6-$NO_2$ | 8-$NO_2$ | $CH_3$ | $CH_3$ | 3 | OH | H | 202–204 | $C_{21}H_{27}N_5O_8$ | 52.83 / 52.80 | 5.70 / 5.90 | 14.67 / 14.55 |
| 82 | 6-$CF_3$ | H | H | H | 3 | OH | H | 188–190 | $C_{20}H_{24}F_3O_4$ | 56.20 / 56.10 | 5.66 / 5.78 | 9.83 / 9.80 |
| 83 | 6-Cl | H | $CH_3$ | $CH_3$ | 3 | O—C(=O)—$(CH_2)_8$—$CH_3$ | H | waxy | $C_{31}H_{46}ClN_3O_5$ | 64.62 / 64.65 | 8.04 / 8.23 | 7.29 / 7.07 |
| 84 | 6-$CF_3$ | $CH_2O$ | H | $CH_3$ | $CH_3$ | 3 | OH | H waxy | $C_{23}H_3F_3N_3O_5$ | 56.9 / 56.6 | 6.23 / 6.03 | 8.66 / 8.60 |

Embodiments of the present invention will be illustrated in the following formulations 1 and 2. The principal ingredient used was 2,2-dimethyl-6-fluoro-1'-[4-(4-hydroxypiperidino)butyl]spiro[chroman-4,4'-imidazolidine]-2',5'-dione hydrochloride.

| Formulation 1: Tablet | |
|---|---|
| principal ingredient | 10.0 parts |
| lactose | 53.5 |
| microcrystalline cellulose | 18.0 |
| corn starch | 18.0 |
| calcium stearate | 0.5 |

The above-mentioned components were mixed together by a conventional method and then granulated. The granules were compression-molded into tablets each weighing 100 mg.

| Formulation 2: Capsule | |
|---|---|
| principal ingredient | 10.0 parts |
| lactose | 70.0 |
| corn starch | 20.0 |

Capsules each weighing 100 mg were prepared by a conventional method according to the above recipe.

We claim:

1. A compound having the formula:

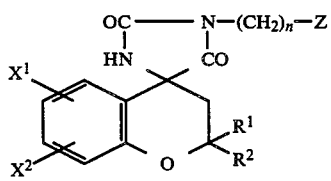

wherein $X^1$ and $X^2$ are the same or different and each represents hydrogen, halogen, lower alkyl, lower alkoxy, trifluoromethyl, trifluoroethoxy or nitro, or $X^1$ or $X^2$ together form a lower alkylenedioxy group which is connected to adjacent carbon atoms in the ring; $R^1$ and $R^2$ are the same or different and each represents hydrogen or lower alkyl, or $R^1$ and $R^2$ together with a single carbon atom to which they are bonded form a $C_5$ or $C_6$ cycloalkyl group; Z is selected from the group consisting of:

(a)

in which $R^3$ and $R^4$ are the same or different and each represents hydrogen, lower alkyl, hydroxyalkyl, carbocyclicaryloweralkyl or carbocyclicaryloweralkyl which is substituted with lower alkoxy, or $R^3$ and $R^4$ together with the nitrogen to which they are bonded form a pyrrolidino or piperidino group, one of the carbon atoms of which may be replaced by an oxygen atom, an imino group, a lower alkylimino group or carbocyclic arylimino group,

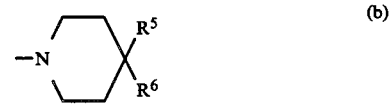

(b)

in which $R^5$ and $R^6$ are the same or different and each represents hydrogen, phenyl or —$OR^7$, wherein $R^7$ is hydrogen, lower alkanoyl, lower alkyl, carbocyclicaryloweralkyl or carbocyclicaryloweralkyl which is substituted with halogen, or $R^5$ and $R^6$ together with the carbon atom to which they are bonded form a 1,3-dioxolan-2-ylene group, or $R^5$ or $R^6$ together form a group of the formula: =O, and

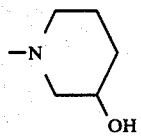 (c)

and n represents an integer of 2 to 7 or a pharmaceutically acceptable acid addition salt thereof.

2. A compound or pharmaceutically acceptable acid addition salt thereof, according to claim 1, wherein Z is

3. A compound or pharmaceutically acceptable acid addition salt thereof, according to claim 1, wherein Z is

4. A compound or pharmaceutically acceptable acid addition salt thereof according to claim 1 wherein Z is

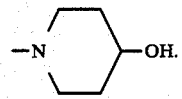

5. A compound according to claim 1 selected from the group consisting of 2,2-dimethyl-6-fluoro-1'-[3-(4-hydroxypiperidino)propyl]spiro[chroman-4,4'-imidazolidine]-2',5'-dione, 6-chloro-2-methyl-1'-[3-(4-phenylpiperidino)propyl]spiro[chroman-4,4'-imidazolidine]-2',5'-dione, 6-chloro-2-methyl-1'-[3-(4-hydroxy-4-phenylpiperidino)propyl]spiro[chroman-4,4'-imidazolidine]-2',5'-dione, 6-fluoro-2-methyl-1'-[3-(4-phenylpiperidino)propyl]spiro[chroman-4,4'-imidazolidine]-2',5'-dione, 6-fluoro-1'-[3-(4-phenylpiperidino)propyl]spiro[chroman-4,4'-imidazolidine]-2',5'-dione, 6,8-dichloro-2,2-dimethyl-1'-[3-(4-hydroxypiperidino)propyl]spiro[chroman-4,4'-imidazolidine]-2',5'-dione, 2,2-diethyl-6-fluoro-1'-[3-(4-hydroxypiperidino)propyl]spiro[chroman-4,4'-imidazolidine]2',5'-dione, 6-chloro-2,2-dimethyl-1'-[3-(4-hydroxypiperidino)propyl]spiro[chroman-4,4'-imidazolidine]-2',5'-dione, 6-chloro-2,2-dimethyl-1'-[4-(4-hydroxypiperidino)butyl]spiro[chroman-4,4'-imidazolidine]-2',5'-dione, 2,2-dimethyl-6-fluoro-1'-[3-(4-hydroxy-4-phenylpiperidino)propyl]spiro[chroman-4,4'-imidazolidine]-2',5'-dione, 6-chloro-1'-[4-(4-acetoxypiperidino)butyl]spiro[chroman-4,4'-imidazolidine]-2',5'-dione, 2,2-dimethyl-6-fluoro-1'-[4-(4-hydroxypiperidino)butyl]spiro[chroman-4,4'-imidazolidine]-2',5'-dione, 2,2-dimethyl-6-fluoro-1'-[3-(4-oxopiperidino)propyl]spiro[chroman-4,4'-imidazolidine]-2',5'-dione, 2,2-dimethyl-6-fluoro-1'-[3-(4-acetoxypiperidino)propyl]spiro[chroman-4,4'-imidazolidine]-2',5'-dione, 2,2-dimethyl-6-fluoro-1'-[3-(4-phenylpiperidino)propyl]spiro[chroman-4,4'-imidazolidine]-2',5'-dione, 2,2-dimethyl-6-fluoro-1'-[3-(4-ethylenedioxypiperidino)propyl]spiro[chroman-4,4'-imidazolidine]-2',5'-dione, 6-chloro-2-methyl-1'-(3-dimethylaminopropyl)spiro[chroman-4,4'-imidazolidine]-2',5'-dione, 6-fluoro-2-methyl-1'-(2-dimethylaminoethyl)spiro[chroman-4,4'-imidazolidine]-2',5'-dione, 6-chloro-2-methyl-1'-(2-diethylaminoethyl)-spiro[chroman-4,4'-imidazolidine]-2',5'-dione, 2,2-dimethyl-6-chloro-(3-dimethylaminopropyl)spiro[chroman-4,4'-imidazolidine]-2',5'-dione, cyclohexane<spiro-2>-6-chloro-1'-(3-dimethylaminopropyl)spiro[chroman-4,4'-imidazolidine]-2',5'-dione, 2,2-dimethyl-6-fluoro-1'-(3-dimethylaminopropyl)spiro[chroman-4,4'-imidazolidine]-2',5'-dione, 2,2-diethyl-6-chloro-1'-(3-dimethylaminopropyl)spiro[chroman-4,4'-imidazolidine]-2',5'-dione, 6-fluoro-2-methyl-1'-(3-dimethylaminopropyl)spiro[chroman-4,4'-imidazolidine]-2',5'-dione, 2,2-dimethyl-6-fluoro-1'-(2-diethylaminoethyl)spiro[chroman-4,4'-imidazolidine]-2',5'-dione, 2,2-dimethyl-6-fluoro-1'-(3-n-propylaminopropyl)spiro[chroman-4,4'-imidazolidine]-2',5'-dione, 2,2-dimethyl-6-fluoro-1'-[3-(3-hydroxyamino)propyl]spiro[chroman-4,4'-imidazolidine]-2',5'-dione, 2,2-dimethyl-6-fluoro-1'-{3-[bis(2-hydroxyethyl)amino]propyl}spiro[chroman-4,4'-imidazolidine]-2',5'-dione, 6-chloro-1'-(3-dimethylaminopropyl)spiro[chroman-4,4'-imidazolidine]-2',5'-dione, 2,2-dimethyl-6-fluoro-1'-{3-[2-(3,4-dimethyloxyphenyl)ethylmethylamino]propyl}spiro[chroman-4,4'-imidazolidine]-2',5'-dione, or a pharmaceutically acceptable acid addition salts thereof.

6. A compound as claimed in claim 1 in which said carbocyclicaryloweralkyl is selected from the group consisting of benzyl, phenethyl and 3,4-dimethoxy phenethyl.

7. A compound as claimed in claim 1 in which Z is $$-N\begin{matrix}R^3\\R^4\end{matrix}$$

wherein $R^3$ and $R^4$ are lower alkyl, $X^1$ is 6-F or 6-Cl, $X^2$ is hydrogen, $R^1$ is hydrogen or lower alkyl, $R^2$ is lower alkyl and n is 2 or 3.

8. A compound as claimed in claim 1 in which Z is

−N⟨ ⟩−OH, $X^1$ is 6-F or 6-Cl, $X^2$ is hydrogen or 8-Cl, $R^1$ and $R^2$ are lower alkyl and n is 3.

9. A compound as claimed in claim 1, in which $X^1$ is 6-Cl, $X^2$ is hydrogen, $R^1$ is $CH_3$, $R^2$ is $CH_3$, n is 3 and Z is

−N⟨ ⟩−OH.

10. An antiarrhythmic composition containing as an active ingredient an antiarrhythmic effective amount of a compound of the following formula or a pharmaceutically acceptable acid addition salt thereof:

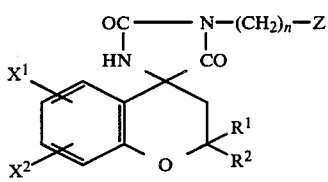

wherein $X^1$ and $X^2$ are the same or different and each represents hydrogen, halogen, lower alkyl, lower alkoxy, trifluoromethyl, trifluoroethoxy, or nitro, or $X^1$ and $X^2$ form a lower alkylenedioxy group connected to adjacent carbon atoms in the ring; $R^1$ and $R^2$ are the same or different and each represents hydrogen or lower alkyl, or $R^1$ and $R^2$ together with the carbon atom to which they are bonded form a $C_5$ or $C_6$ cycloalkyl group; Z is selected from the group consisting of:

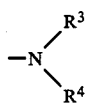 (a)

in which $R^3$ and $R^4$ are the same or different and each represents hydrogen, lower alkyl, hydroxylalkyl, carbocyclicarylloweralkyl or carbocyclicarylloweralkyl which is substituted with lower alkoxy, or $R^3$ and $R^4$ together with the nitrogen atom to which they are bonded form a pyrrolidino or piperidino group, one of the carbon atoms of which may be replaced by an oxygen atom, an imino group, a lower alkylimino or carbocyclic arylimino group,

 (b)

in which $R^5$ and $R^6$ are the same or different and each represents hydrogen, phenyl or $—OR^7$, wherein $R^7$ is hydrogen, lower alkanoyl, lower alkyl, carbocyclicarylloweralkyl or carbocyclicarylloweralkyl which is substituted with halogen, or $R^5$ and $R^6$ together with the carbon atom to which they are bonded form a 1,3-dioxolan-2-ylene group, or $R^5$ and $R^6$ together form a group of the formula: $=O$, and

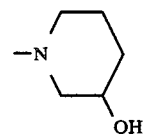 (c)

and n represents an integer of 2 to 7, in combination with a pharmaceutically acceptable vehicle.

11. A method of treating a patient afflicted with arrhythmia which comprises administering to the patient a therapeutically effective amount of an antiarrhythmic composition as claimed in claim 10.

* * * * *